United States Patent
Strukov et al.

(10) Patent No.: US 9,827,273 B2
(45) Date of Patent: Nov. 28, 2017

(54) PREPARATION AND METHOD FOR THE PROPHYLAXIS AND TREATMENT OF ATYPICAL OSTEOPOROSIS

(76) Inventors: Villorij Ivanovich Strukov, Penza (RU); Olga Jhones, Fort Worth, TX (US); Evgenij Nikolaevich Krutiakov, Penza (RU); Konstantin Gennad'evich Elistratov, Penza (RU)

( * ) Notice: Subject to any disclaimer, the term of this patent is extended or adjusted under 35 U.S.C. 154(b) by 0 days.

(21) Appl. No.: 14/395,478

(22) PCT Filed: Aug. 21, 2012

(86) PCT No.: PCT/RU2012/000687
§ 371 (c)(1),
(2), (4) Date: Mar. 9, 2015

(87) PCT Pub. No.: WO2013/157982
PCT Pub. Date: Oct. 24, 2013

(65) Prior Publication Data
US 2015/0224150 A1  Aug. 13, 2015

(30) Foreign Application Priority Data

Apr. 19, 2012 (RU) ................. 2012115654

(51) Int. Cl.
| | | |
|---|---|---|
| *A61K 35/64* | (2015.01) | |
| *A61K 31/592* | (2006.01) | |
| *A61K 31/593* | (2006.01) | |
| *A61K 45/06* | (2006.01) | |
| *A61K 35/63* | (2015.01) | |

(52) U.S. Cl.
CPC ............ *A61K 35/64* (2013.01); *A61K 31/592* (2013.01); *A61K 31/593* (2013.01); *A61K 35/63* (2015.01); *A61K 45/06* (2013.01)

(58) Field of Classification Search
None
See application file for complete search history.

(56) References Cited

U.S. PATENT DOCUMENTS

2006/0252045 A1* 11/2006 Chatterjee-Kishore ............... C12Q 1/6876
435/6.13

FOREIGN PATENT DOCUMENTS

RU  2412616 C1 *  2/2011
RU  2412616 Y    2/2011

OTHER PUBLICATIONS

"Handbook for a Beekeeper" (http://great-beemaster.blogspot.com/2013/05/drone-brood.html)—accessed Sep. 2015.*
PROMT translation of paragraph 32 of RU 2412616 (http://www.online-translator.com/—accessed Nov. 2015).*
Kaltsii—DZ Nikomed forte, Dec. 29, 2006.
Kaltsii—vitamin D i ego metabolity v lechenii osteoporoza, Feb. 1, 2010.
Izvestnye i novye tekhnologii v lechenii i profilaktiki osteoporoza. Osteomed—effektivnyi reguliator kaltsievogo obmena Aug. 2012.
International Search Report PCT/RU2012/000687, Feb. 7, 2013 (1 pg.).

* cited by examiner

*Primary Examiner* — Susan Hoffman
(74) *Attorney, Agent, or Firm* — Patentagar PLLC; Alexander Rabinovich

(57) ABSTRACT

The invention related to medicine, in particular, to a method and a preparation for preventing and treating atypical osteoporosis with normal or increased bone tissue mineralization with the presence of cavities in trabecular bone sections (and conditions similar thereto involving excess mass and metabolic syndrome). The method comprises administrating a preparation comprising from 10 mg and 1000 mg of drone brood per day and from 50 IU and 100,000 IU of vitamin D or vitamins of the group D and/or active metabolites thereof per day. The preparation comprising drone brood and vitamin D or vitamins of the group D and/or active metabolites thereof can be in a powder, tablet or capsule form. The method and the preparation provide redistributing calcium in the body, reducing mineralization of soft tissues, vessels and other organs, and filling cavities in trabecular bone.

2 Claims, 7 Drawing Sheets

PREPARATION AND METHOD FOR THE PROPHYLAXIS AND TREATMENT OF ATYPICAL OSTEOPOROSIS

The invention relates to medicine and in particular to agents for the treatment and prevention of conditions associated with various forms of osteoporosis, particularly involving metabolic syndrome.

The prior art discloses that, in connection with the discovery of D vitamins and the subsequent hormonal forms of vitamin D, the focus for treating opsteopenia, osteoporosis and osteomalacia shifted to this group of preparations (cholecalciferol, ergocalciferol, videhol, vigantol, One-Alpha, catcitriol, etc.). Calcium and vitamin D preparations were combined to enhance calcium absorption. Medications such as 'Kaltsii D3 Nikomed', 'Kaltsimen Advans', 'Kaltsimin', 'Tsitrokal', 'Alfadol kaltsiya' etc. are now widely used.

The disadvantage of these agents is that:

1) Preparations of calcium and vitamin D intensify the activity of one another, and therefore there is a great risk of over mineralising various tissues and organs to the point of calcinosis, i.e. irreversible changes in the body of the patient. Uncontrolled use of calcium preparations may result in a drug-induced pathology, the calcification of small and large vessels, the formation of kidney stones as well as stones in other organs.

2) There already are counter indications against the use of these products, such as kidney stones, gall stones and hypercalcemia etc.

Osteoporosis is a metabolic skeletal disease which is characterised by a reduction in bone mass per unit volume and by the microarchitectural deterioration of bone tissue, which lead to a reduction in the amount of calcium in the bones and to a high fracture risk for any bone including the hip.

The prior art doe's not disclose, and this document has established, that deterioration and restoration of bone tissue mineralization happen unevenly. Thus, in postmenopausal osteoporosis bone density is first lost in trabecular sections and is then lost in cortical bone sections. Appropriate therapy can successfully cure osteoporosis. In addition, restoring the structure is not even process and happens in reverse order. There are many clinical forms of osteoporosis, which can be systemic with a uniform bone lesion or with a primary lesion on separate parts of the skeleton such as vertebral bodies, limbs, etc. However, the same treatment regimes are generally recommended for all forms of osteoporosis.

Consequently, interest in hormonal mechanisms for regulating bone tissue mineral density has risen significantly.

It is known that D hormone (the metabolites of vitamin D) plays an important role in maintaining bone mineral density in both young and old people. Low levels of testosterone and D hormone are one of the causes of osteoporosis, and consequently a reduction in bone mineral density in men is a risk factor for bone fractures.

Bisphosphonates are used to treat reduced bone density and osteoporosis. However, it has been proven that the effectiveness of these preparations is minimal if D hormone and testosterone levels are depressed because they provide for the proper absorption of preparations aimed at restoring bone density. Therefore, treatment for bone density deterioration must be comprehensive and aimed at restoring the deficiency (where there is one) of testosterone and at absorbing the calcium preparations.

The disadvantage of these preparations is that there are problems with preparations that maintain testosterone levels in the body (for example, testosterone propionate). The body produces even less of its own testosterone when testosterone is supplied to the body from an outside source.

The problem of increasing bone mineral density has been addressed with the aid of the agent 'Osteomed', a compound of between 10 wt. % and 95 wt. % calcium and between 5 wt. % and 90 wt. % drone brood (U.S. Pat. No. 2,412,616, A23L1/30, 2009). The introduction of drone brood is explained below. Drone brood is a donor of the following entomological sex hormones: prolactin, estradiol, progesterone and testosterone, which stimulate the reproductive functions in men and women. Drone brood, which is saturated with hormones and vitamins that are not hormonal replacement, is effective for hormone imbalance, stimulates the central mechanisms regulating androgen formation intensity and eliminates the possibility of replacement therapy.

The following is the disadvantage of the known agent:

'Osteomed' contains a calcium compound. There is a great deal of calcium in patients with hypermineralization, and calcium deposits have even been observed in their soft tissues (muscles). It is strongly recommended that these patients do not take calcium preparations. However, the authors found that these patients have trabecular bone cavities which can cause fractures, particularly if they have a history of this problem. This result was found by the authors and was not previously known. Therefore, these patients should not take 'Osteomed'.

Figure 1:
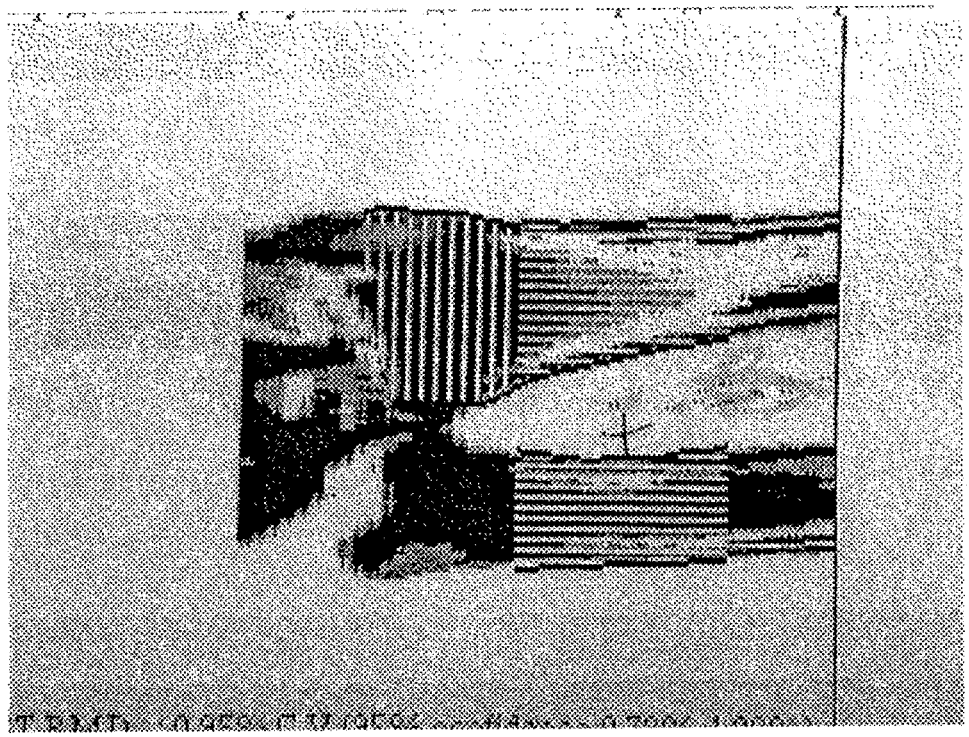
FIG. 1 is a X-ray bone densitometry screenshot before treatment with the preparation according to Example 1.

The technical result of the claimed invention consists in creating an agent that can facilitate the redistribution of calcium in the body: reducing mineralization in soft tissues, vessels and other organs, and which could also facilitate the filling of trabecular bone cavities.

This result is achieved in that in the method for preventing and treating atypical osteoporosis with normal or increased bone tissue mineralization with the presence of cavities in trabecular bone sections (and conditions similar thereto involving excess mass and metabolic syndrome), involves taking between 10 mg and 1000 mg per day of drone brood, between 50 IU and 100,000 IU per day of vitamin D or vitamins of this group and/or the active metabolites thereof; and a preparation for the prevention and treatment of atypical osteoporosis with normal or increased bone tissue mineralization with the presence of cavities in trabecular bone sections (and conditions similar thereto involving excess mass and metabolic syndrome), which consists of between 10 mg and 1000 mg of drone brood and between 50 IU and 100,000 IU of vitamin D or vitamins of this group and/or the active metabolites thereof, and according to the invention drone brood, vitamin D or vitamins of this group and/or the active metabolites thereof are supplied to the body at the same time daily, and the preparation is provided in powder, tablet or capsule form.

The method for preventing and treating atypical osteoporosis with normal or increased bone mineral density with the presence of cavities in trabecular bone sections (and conditions similar thereto involving excess mass and metabolic syndrome) is carried out in the following way.

In order to solve the problem of interest, the authors have created and tested on volunteers an agent in a composition with the ratio of ingredients:

between 50 IU and 100,000 IU per day of vitamin D or vitamins of this group (and/or the active metabolites thereof); and between 10 mg and 1000 mg per day of drone brood.

The claimed agent can be provided in powder, tablet or capsule form.

Vitamin D is included because drone brood is saturated with vitamins in particular vitamin D3, but in non-replacing, small doses. Therefore, the concentration thereof is insufficient for treating osteoporosis.

Drone brood has to be introduced as a donor of the following sex hormones: estradiol, progesterone and testosterone, which have a positive effect on bone mineralization.

The scope of the range of the claimed preparation is determined by the characteristics of the patient: their age, eating habits, lifestyle, race, country of habitation, sex and genetic and previous diseases. A doctor assessing these criteria selects the specific proportion of the constituent parts of the claimed agent and adjusts this based on a change regarding cavity closures.

An explanation of the range limits:

1) Between 50 IU and 100,000 IU per day of vitamin D or vitamins from this group (and/or the active metabolites thereof). The lower end is the effective dose while the upper end is a toxic dose.

2) Between 10 mg to 1000 mg per day of drone brood. The lower end is the effective dose while the upper end is the feasibility of use in terms of the ratio of effectiveness/price rise of the product.

The studies have established that using the claimed preparation strengthens the mechanism for the uniform restoration of bone mineral density, the use of drone brood in combination with vitamin D additionally aims to enhance the remodelling of injured bone tissue sections and for bone tissue retention by maintaining androgen levels.

The combined use of vitamin D with drone brood makes it possible to achieve the greatest effectiveness in osteoporosis therapy in patients with hypercalcaemic conditions, to reduce the frequency of adverse side effects in the form of calcified deposits and stones forming in the kidneys and in other organs.

Although the components of the claimed preparation are known in folk and traditional medicine, the combination thereof in one product is not known, specifically, the discovered synergistic effect makes it possible to solve the problem of balanced bone mineralization in both trabecular bone sections and cortical bone sections and to solve the problem of interest and to achieve the claimed technical result, namely to eliminate or reduce an imbalance in the mineralization of various bone tissue sections.

Examples of closing cavities using the homogenate of drone brood and vitamin D3 in patients with hypermineralization:

Example No. 1: Patient FAD. 64 years of age with postmenopausal osteoporosis. The patient took 'Kaltsii D3 forte' made by the company 'NIKOMED' for a year. She has been diagnosed with hypermineralization, salt deposits in her soft tissues. Despite this condition, the patient has cavities. She was prescribed treatment with the claimed agent in a composition in the form of a powder mixture: 1000 mg of drone brood+100 IU of vitamin D3 per day.

The results before and after treatment are shown in FIG. 1.

The picture of the beginning of treatment clearly shows salt deposits in soft tissues, which indicates hypermineralization. These are orange in the picture on a white background between two bones.

Figure 2:
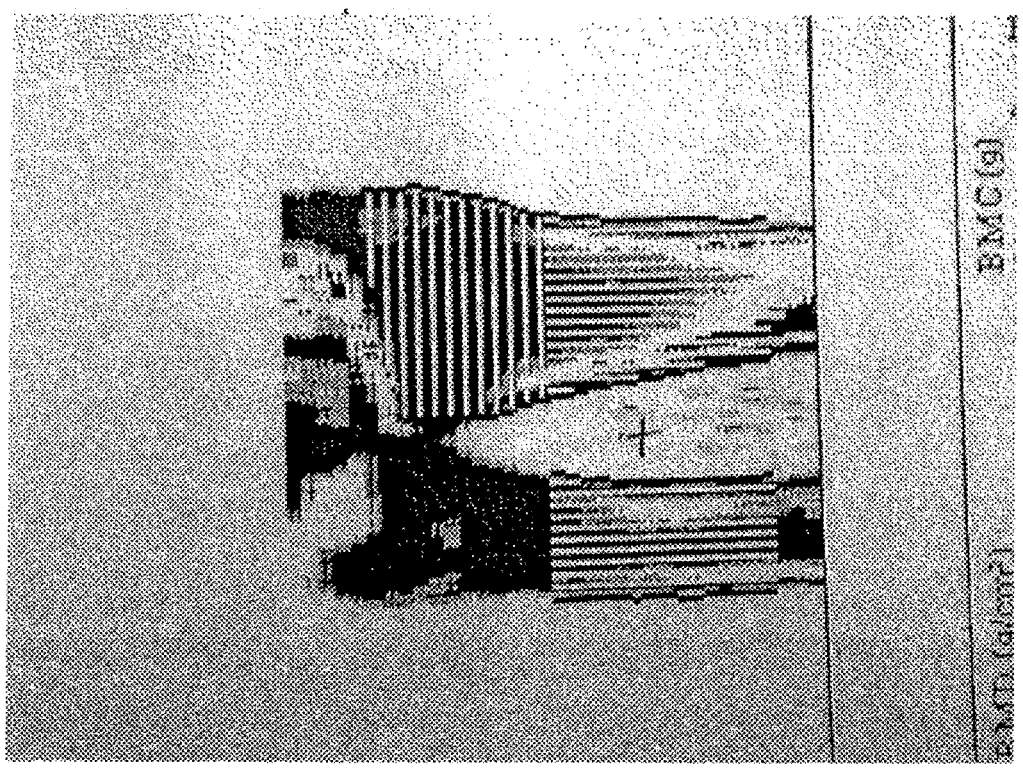
FIG. 2 is a X-ray bone densitometry screenshot after 9 months of treatment with the preparation according to Example 1.

The results after 9 months of treatment are shown in FIG. 2.

It can be seen that the claimed agent reduces salt deposits and closes the cavities. In other words, the calcium was redistributed within the body.

Example No. 2. Female patient Z. 66 years old with postmenopausal osteoporosis. The patient took 'Kaltsii D3 forte' made by the company 'NIKOMED' for 9 months. She has been diagnosed with hypermineralization, salt deposits in her soft tissues. Despite this condition, the patient has cavities. She was prescribed treatment with the claimed agent in a composition in the form of a powder mixture: 500 mg of drone brood+2500 IU of vitamin D3 per day.

Figure 3:
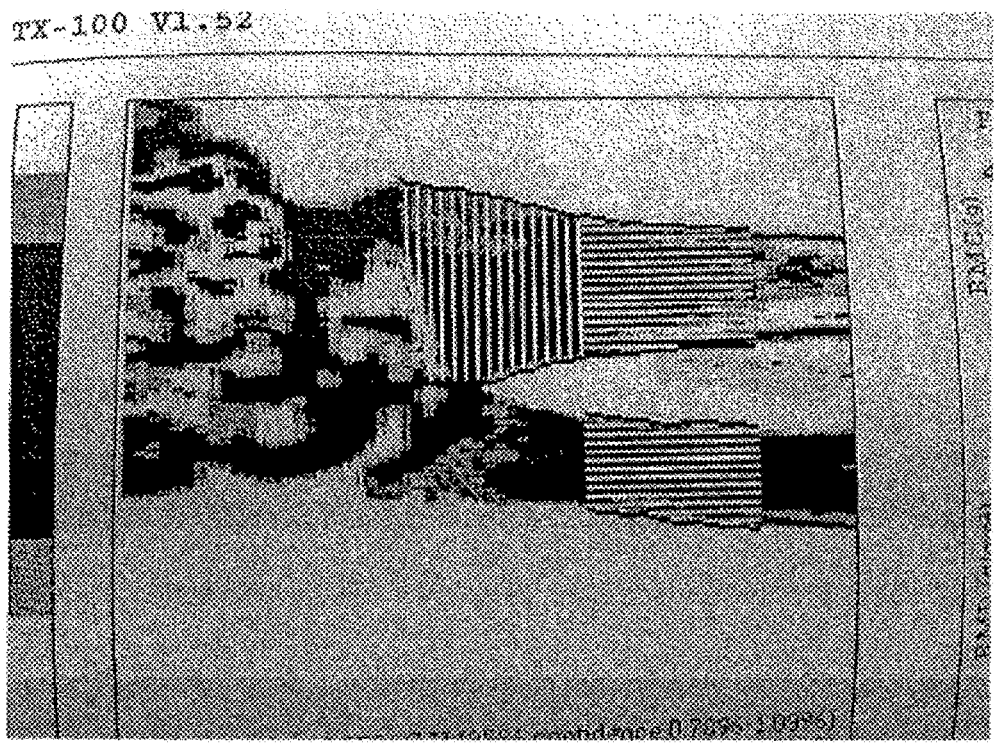
FIG. 3 is a X-ray bone densitometry screenshot before treatment with the preparation according to Example 2.

The results before and after the 6 month course of treatment are shown in FIG. 3, 4.

The results before treatment with the claimed mixture are shown in FIG. 3.

Figure 4:
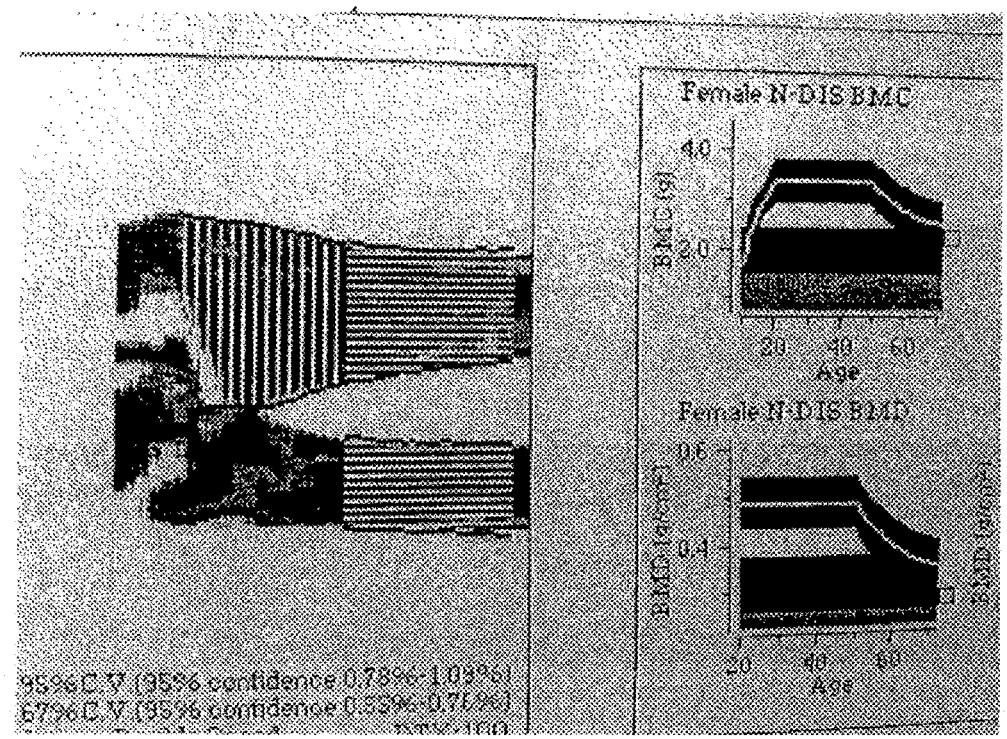
FIG. 4 is a X-ray bone densitometry screenshot after 6 months of treatment with the preparation according to Example 2.

The results after a six-month treatment with the claimed mixture are shown in FIG. 4.

The cavities were reduced and the salt deposits in the soft tissues disappeared.

Example No. 3. Female patient Z 1. 70 years old with postmenopausal osteoporosis. The patient took 'Kaltsii D3 forte' made by the company 'NIKOMED' for 12 months. She has been diagnosed with hypermineralization, salt deposits in her soft tissues. Despite this condition, the patient has large cavities. She was prescribed treatment with the claimed agent in a composition in the form of a powder mixture: 500 mg of drone brood+100,000 IU of vitamin D2 per day.

Figure 5:
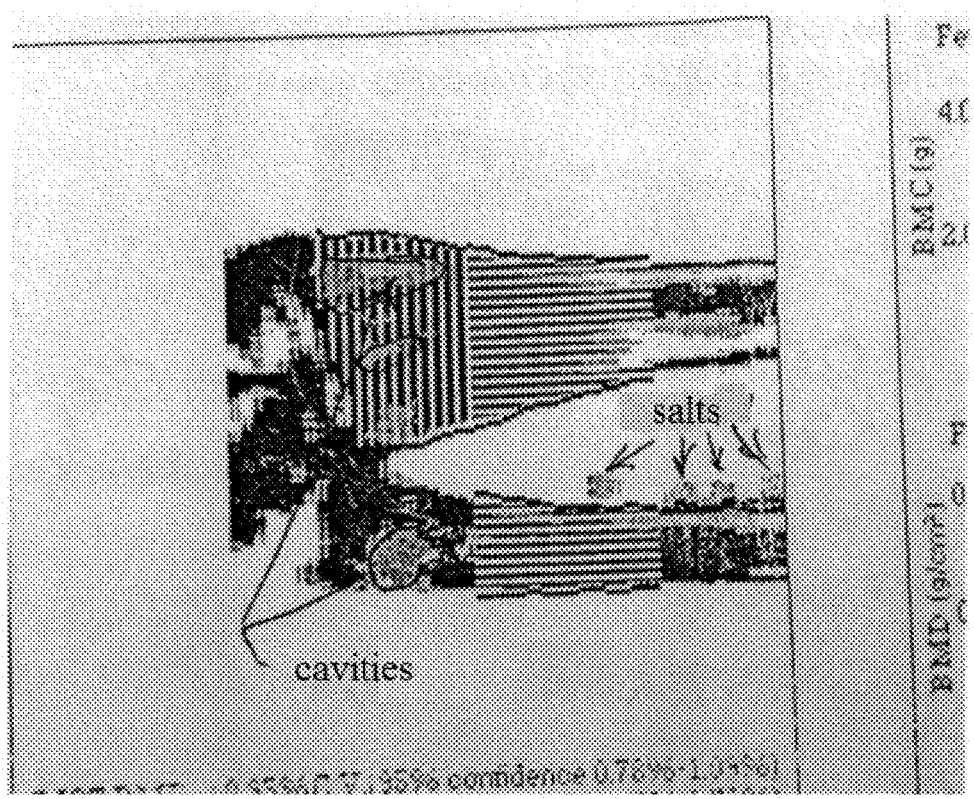
FIG. 5 is a X-ray bone densitometry screenshot before treatment with the preparation according to Example 3.

The results before and after the 6 month course of treatment are shown in FIG. 5, 6.

The results before treatment with the claimed mixture are shown in FIG. 5.

Figure 6:
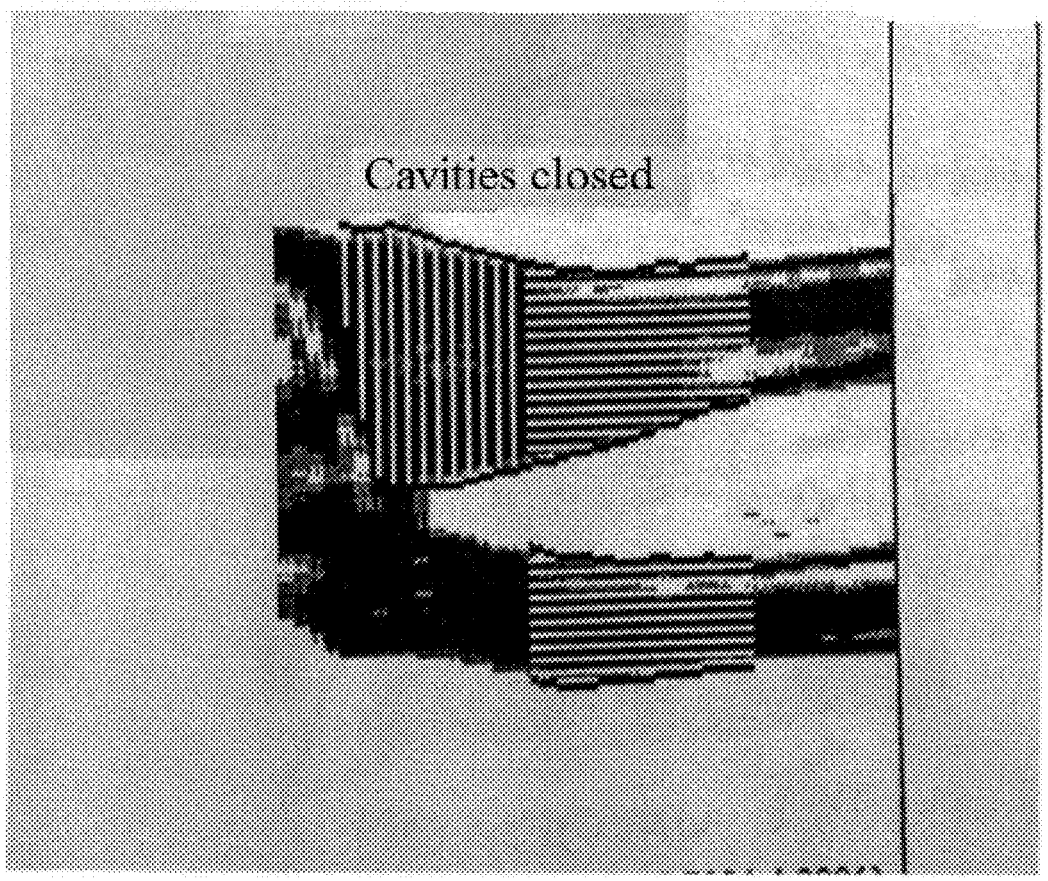
FIG. 6 is a X-ray bone densitometry screenshot after 6 months of treatment with the preparation according to Example 3.

The results after treatment with the claimed mixture are shown in FIG. 6.

As the picture shows, the cavities closed, but the salt deposits in the soft tissues did not completely disappear, which indicates a large dose of vitamin D2 for this patient.

Regarding the range for using vitamin D and the active metabolites thereof, it should be noted that various forms of vitamin D have various degrees of therapeutic activity. Thus, vitamin D2 is weaker than vitamin D3, and therefore a greater amount of D2 is required in comparison to vitamin D3. The same is true regarding vitamin D metabolites.

Example No. 4: The ineffectiveness of the claimed agent is lower than the low limit: Female patient D. 60 years of age with postmenopausal osteoporosis. The patient took 'Kaltsii D3 forte' made by the company 'NIKOMED' for 6 months. She has been diagnosed with hypermineralization, salt deposits in her soft tissues. She does not have any cavities.

She was prescribed treatment with the claimed agent in a composition in the form of a powder mixture: 9 mg of drone brood+40 IU of vitamin D2 per day.

Figure 7:
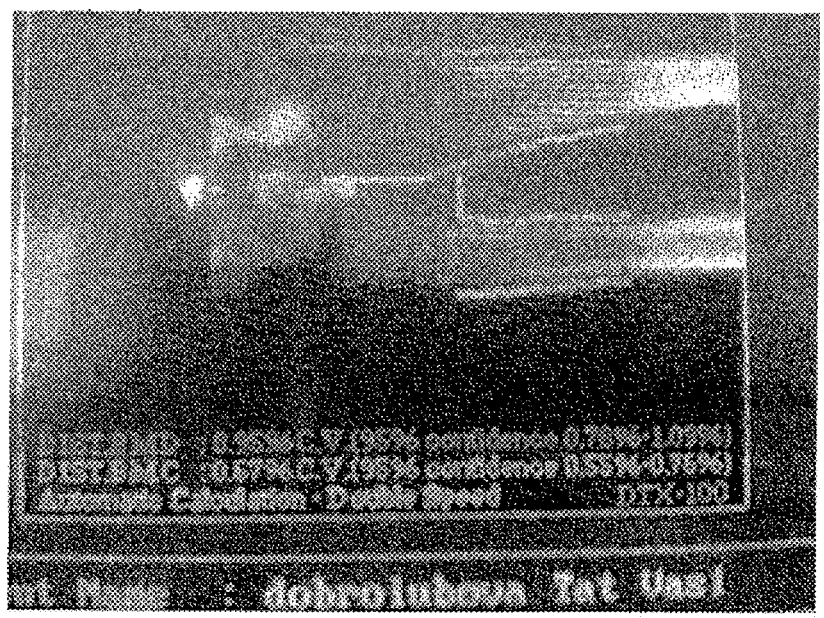
FIG. 7 is a X-ray bone densitometry screenshot before treatment with the preparation according to Example 4.

The results before and after the 6 month course of treatment are shown in FIG. 7, 8.

The results before treatment with the claimed mixture are shown in FIG. 7.

Figure 8:
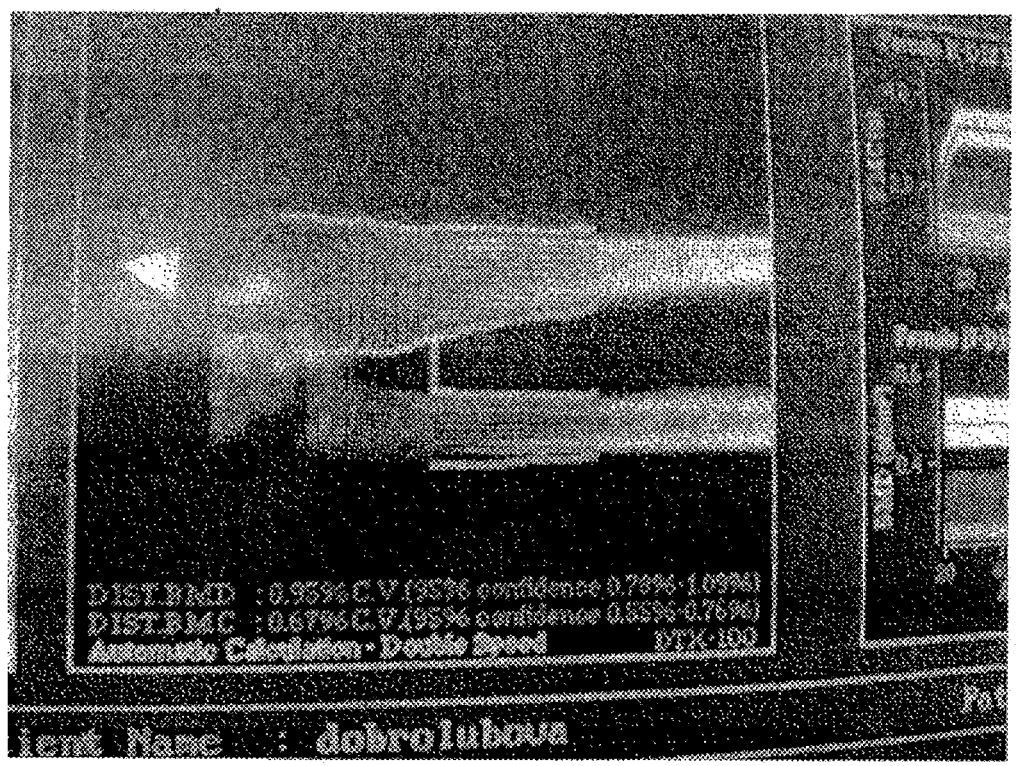
FIG. 8 is a X-ray bone densitometry screenshot after 6 months of treatment with the preparation according to Example 4.

The results after treatment are shown in FIG. 8.

CONCLUSION there are no significant changes, the bone mineral density has been reduced, the mineral deposits have also proportionally reduced.

When prescribing the claimed agent, the doctor chooses the dosage of the constituent parts thereof individually based on the condition of the disease of the patient. The condition of the patient should be assessed with the aid of density measuring apparatuses measuring the cavities every 6-9 months and adjusting the composition of the claimed agent used.

We claim:

1. A method for preventing or treating atypical osteoporosis with normal or increased mineralization of bone tissue and the presence of cavities in trabecular bone sections, comprising the steps of:

a) providing drone brood and at least one ingredient selected from the group consisting of vitamins of the group D and active metabolites thereof and b) administering to a patient in need the drone brood in an amount of from 10 mg to 1000 mg per day and the at least one ingredient selected from the group consisting of vitamins of the group D and active metabolites thereof in an amount of from 50 IU to 100,000 IU per day.

2. The method according to claim 1 wherein the drone brood and the at least one ingredient selected from the group consisting of vitamins of the group D and active metabolites thereof are administered simultaneously.

* * * * *

UNITED STATES PATENT AND TRADEMARK OFFICE
CERTIFICATE OF CORRECTION

PATENT NO. : 9,827,273 B2
APPLICATION NO. : 14/395478
DATED : November 28, 2017
INVENTOR(S) : Strukov et al.

It is certified that error appears in the above-identified patent and that said Letters Patent is hereby corrected as shown below:

On the Title Page

Item (73) should read:
Parapharm LLC, Penza, Russian Federation

Signed and Sealed this
Tenth Day of April, 2018

Andrei Iancu
*Director of the United States Patent and Trademark Office*